United States Patent [19]

Schoenberger et al.

[11] Patent Number: 5,399,319
[45] Date of Patent: Mar. 21, 1995

[54] APPARATUS FOR FILTERING AIR AND FOR CREATING A POSITIVE/NEGATIVE PRESSURE

[75] Inventors: Stephen B. Schoenberger, Northbrook, Ill.; Robert M. Reavis, Kansasville, Wis.

[73] Assignee: Vector Technologies Ltd., Milwaukee, Wis.

[21] Appl. No.: 100,777

[22] Filed: Aug. 2, 1993

[51] Int. Cl.[6] .................. A61L 9/20; B01D 29/11; B01D 46/54
[52] U.S. Cl. ..................... 422/121; 55/279; 55/385.2
[58] Field of Search .............. 422/4, 5, 121, 122, 422/24, 117; 55/279, 497, 498, 472, 385.2

[56] References Cited

U.S. PATENT DOCUMENTS

| | | | |
|---|---|---|---|
| 3,630,174 | 12/1971 | Runkle et al. | 119/15 |
| 4,118,191 | 10/1978 | Böhnensieker | 55/279 |
| 4,210,429 | 7/1980 | Golstein | 422/121 X |
| 4,988,372 | 1/1991 | Meline | 55/498 X |
| 5,074,894 | 12/1991 | Nelson | 422/121 X |
| 5,203,989 | 4/1993 | Reidy | 55/279 X |
| 5,213,595 | 5/1993 | Kim | 55/385.2 X |
| 5,225,167 | 7/1993 | Wetzel | 422/121 |
| 5,259,854 | 11/1993 | Newman | 55/472 X |

OTHER PUBLICATIONS

Red Baron "Hepa-Vent" System-Aug. 1990.
"Two Good Reasons to Buy The Twinn 22."-Dec. 1990.
Coppus PFX-1500 Portable Filtration Unit-1992.
NSA 7100B Environmental Air System-1991.

*Primary Examiner*—Robert J. Warden
*Assistant Examiner*—E. Leigh Dawson
*Attorney, Agent, or Firm*—Michael, Best & Friedrich

[57] ABSTRACT

A portable, convertible apparatus for creating either a negative pressure or a positive pressure in and filtering the air in a room, the apparatus comprising a housing having upper and lower ends. The housing defines an air flow path between the upper and lower ends and contains, within the air flow path, a HEPA filter and a fan. A dome-shaped inlet grille is mounted on the upper end of the housing, and a cylindrical outlet grille is mounted on the lower end of the housing. The apparatus also includes an annular cover for the outlet grille, which cover is adapted to communicate with the exterior of the room, and a dome-shaped cover for the inlet grille, which cover is adapted to communicate with the exterior of the room. The apparatus creates a negative pressure in the room when the annular cover is placed over the outlet grille and the dome-shaped cover is removed, and creates a positive pressure in the room when the annular cover is removed and the dome-shaped cover is placed over the inlet grille.

19 Claims, 1 Drawing Sheet

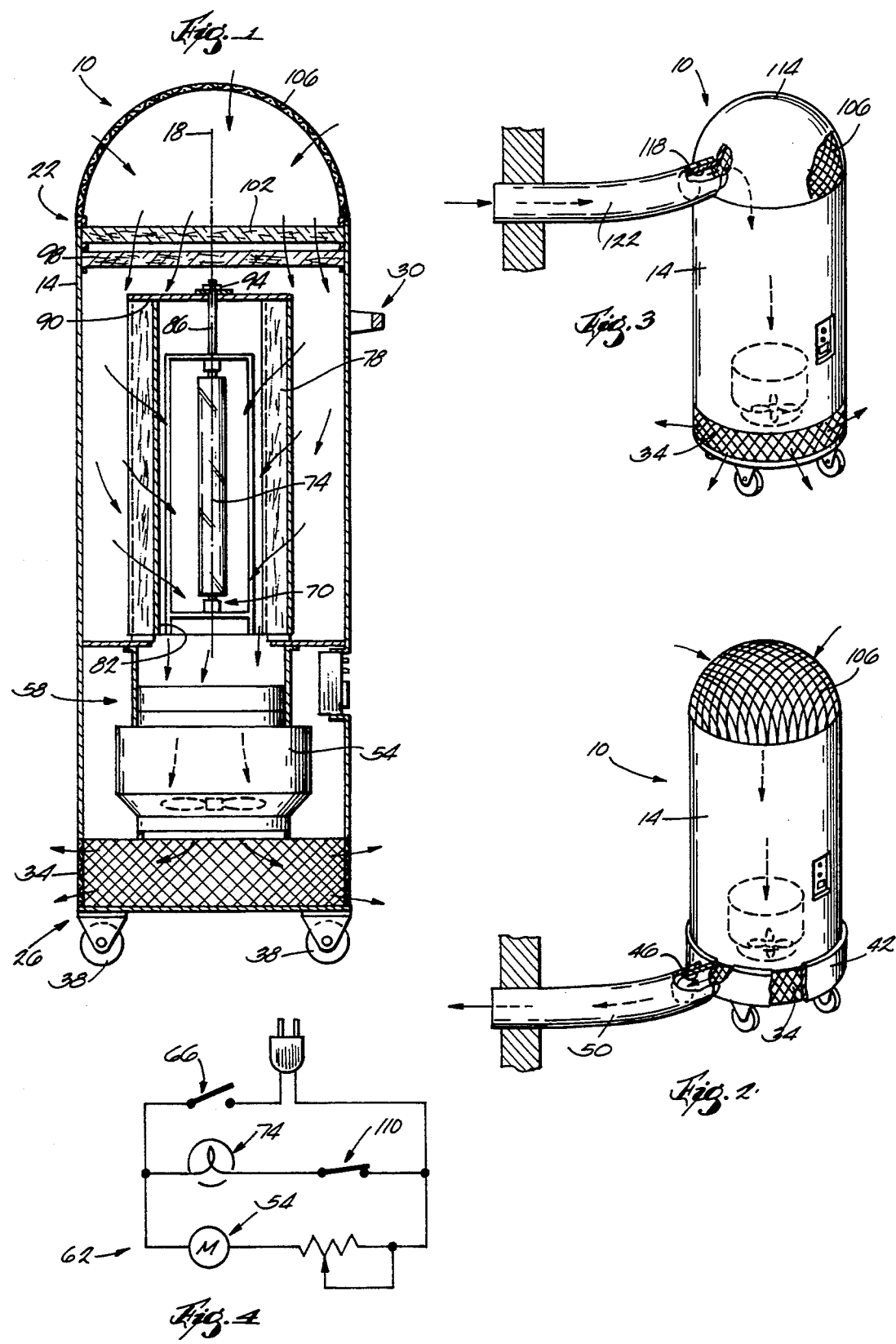

APPARATUS FOR FILTERING AIR AND FOR CREATING A POSITIVE/NEGATIVE PRESSURE

BACKGROUND OF THE INVENTION

The invention relates to apparatus for filtering air and to apparatus for creating a positive pressure or a negative pressure in a room.

In some circumstances it is desirable to filter the air in a room to remove therefrom infectious airborne particles such as tuberculosis nuclei. This is particularly important in hospital patient rooms, in operating rooms and in home health care situations. However, simple filtering of the air is sometimes insufficient to protect against the spread of disease. Accordingly, it may be necessary to regulate the pressure in the room to achieve the desired result.

Specifically, in hospital patient rooms and home health care rooms, the air in the rooms may already be contaminated. Thus, it is desirable to prevent air in the room from escaping to other rooms in the hospital or home. Allowing the air in the rooms to escape could contaminate the air in other adjacent rooms. One known method of achieving this result is to create a negative pressure in the room relative to the pressure in the adjacent rooms. Thus, if the door to the room is opened, clean air will follow the pressure gradient and will rush into the patient room from the adjacent room or rooms. The inrush of clean air substantially prevents contaminated air from leaving the room and thereby prevents the contamination of the air in the adjacent rooms.

Alternatively, in operating rooms and in other sterile environments, the clean air is already in the operating room and the goal is to prevent contaminated outside air from entering the operating room. Accordingly, a positive pressure is created in the operating room relative to the pressure in adjacent rooms so that if a door opens, clean air will rush out of the operating room thereby substantially preventing contaminated air from rushing into the operating room.

Known systems for effecting these results are typically highly complex and extremely expensive. Moreover, a system installed to create only a negative pressure, or alternatively only a positive pressure, is inherently limited to that particular task and may be limited to operation in a particular room. These limitations restrict the ability of the patient to move from room to room or the ability of the hospital to utilize the room for different kinds of patients or procedures.

SUMMARY OF THE INVENTION

Accordingly, it is desirable to provide a portable apparatus that is capable of removing infectious airborne particles from the air in a room, that is capable of creating a negative pressure in the room and that is convertible so that it is alternatively capable of creating a positive pressure in the room.

The invention provides a portable apparatus for creating either a negative pressure or a positive pressure in and filtering the air in a room. The apparatus includes a generally cylindrical housing having a generally vertical axis and upper and lower ends. A housing defines an air flow path between the upper and lower ends, and contains, within the airflow path, an annular, cartridge-type HEPA filter with a lower end having therein an outlet. A prefilter is located above the annular filter and a UV light source is located inside the annular filter.

The apparatus also includes a fan mounted in the housing below the outlet of the annular filter.

The apparatus includes a dome-shaped inlet grille mounted on the upper end of the housing and centered on the housing axis. The apparatus also includes a removable dome-shaped cover for the inlet grille, which cover is adapted to communicate with the air flow path and is connected to an inlet conduit communicating with the exterior of the room. The apparatus also includes an outlet grille adjacent the lower end of the housing. A removable outlet cover is adapted to be mounted on the outlet grille and is connected to an outlet conduit, which conduit communicates with the exterior of the room. Rollers are mounted on the lower end of the housing to support the apparatus for movement on the floor of the room.

When the outlet cover is mounted on the outlet grille, air flows from the room into the housing through the inlet grille, through the prefilter, through the annular filter in close proximity to the UV light source, through the annular filter outlet, and through the outlet conduit to the exterior of the room to filter the air exiting the room and create a negative pressure in the room.

Alternatively, when the outlet cover is removed from the outlet grille and the inlet cover is mounted on the inlet grille, air flows from the exterior of the room into the housing through the inlet grille, through the prefilter, through the annular filter in close proximity to the UV light source, through the annular filter outlet, through the outlet grille and into the room to filter the air entering the room and create a positive pressure in the room.

A principal feature of the invention is the provision of a portable apparatus for creating a negative pressure in and filtering the air in a room.

Another feature of the invention is the provision of a portable apparatus for creating a negative pressure in and filtering the air in a room, which apparatus is convertible to an apparatus for creating a positive pressure in and filtering the air in a room.

Another feature of the invention is the provision of such an apparatus which is inexpensive, lightweight, quiet and portable such that it is appropriate for use in a hospital patient room, home health care room or operating room.

Other features and advantages of the invention will become apparent to those of ordinary skill in the art upon review of the following detailed description, claims, and drawings.

DESCRIPTION OF THE DRAWINGS

FIG. 1 is a cross-sectional view of an apparatus embodying the invention.

FIG. 2 is a view showing the apparatus with the outlet cover mounted on the outlet grille to create a negative pressure in the room.

FIG. 3 is a view similar to FIG. 2 showing the apparatus with the inlet cover mounted on the inlet grille to create a positive pressure in the room.

FIG. 4 is a schematic view of the power circuit of the apparatus.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Shown in FIG. 1 of the drawings is a portable filtering apparatus 10 for filtering the air passing through the apparatus 10 and for creating a negative pressure in a room. The apparatus 10 is convertible to alternatively create a positive pressure in a room. Preferably, the apparatus 10 has a weight of less than one hundred pounds, has a height of six feet or less and has a diameter of less than two feet. The illustrated apparatus 10 has a weight of seventy-five pounds, a height of five feet and a diameter of eighteen inches.

The apparatus 10 includes a generally cylindrical housing 14 having a vertical axis 18 and upper and lower ends 22 and 26. The housing 14 defines an air flow path between the upper and lower ends 22 and 26 and has at least one handle 30 mounted thereon to allow the apparatus 10 to be easily moved.

The lower end 26 of the housing 14 includes a generally cylindrical outlet grille 34. The outlet grille 34 provides a three hundred and sixty degree exhaust to reduce air turbulence at the outlet. The outlet grille 34 is preferably formed from a sheet of punched metal. The lower end 26 can have therein a foam pad (not shown) to dampen any noise emanating from the outlet. Four casters or rollers 38 are mounted on the lower end 26 to support the apparatus 10 on the floor and allow the unit to be easily rolled, thereby making the unit portable. Alternatively, the housing 14 can be mounted on extendible legs (not shown) that allow the height of the apparatus 10 to be adjusted to the applicable breathing zone.

The apparatus 10 also includes (see FIG. 2) a removable annular outlet cover 42 for covering the outlet grille 34. The annular cover 42 includes a cover outlet 46 which communicates with an outlet conduit 50 communicating with the exterior of the room. The cover 42 is used to create a negative pressure in a room in a manner which will be described below in greater detail.

A fan 54 is mounted in the housing 14 above and adjacent to the cylindrical outlet grille 34. As is known in the art, the fan 54 is connected to the housing 14 using a conventional isolation mount 58. The isolation mount 58 reduces the noise and vibration which might otherwise be created by the fan 54. The fan 54 is preferably a reverse incline fan and is capable of operating at variable speeds, making the apparatus 10 effective in different sized rooms. Also, the fan 54 preferably has a capacity of 750 cubic feet per minute. In any event, the fan 54 should be able to provide, in a standard hospital room, the minimum air changes required by guidelines of the Center for Disease Control.

The fan 54 is electrically connected to a power circuit 62 (see FIG. 4) which is adapted to be connected to conventional residential 120 volt alternating current power. The circuit includes an on/off switch 66 mounted on the exterior of the housing 14. The power switch 66 preferably includes an accompanying power light (not shown) to indicate whether the unit is "on" or "off".

The apparatus 10 also includes an elongated ultraviolet (UV) light fixture 70 which is mounted above the fan 54. A UV or natural florescent light 74 is installed in the fixture so that the light 74 extends vertically upward from the fan 54 along the housing axis 18. The light fixture 70 is also electrically connected to the power circuit 62. As will be described in more detail below, means are provided to prevent activation of the UV light 74 during servicing of the filtering apparatus 10.

The apparatus 10 also includes an annular, cartridge-type disposable HEPA (high efficiency particulate air) filter 78 mounted in the housing 14. The HEPA filter 78 includes a lower end defining an outlet 82. The filter 78 surrounds the UV light 74 and creates a cavity around the light 74, which cavity partially defines the air flow path. Preferably, the filter 78 removes 99.97% of all particles that are three/tenths of a micron or larger.

Means are provided in the apparatus 10 for detecting and subsequently indicating whether there is inadequate air flow through the HEPA filter 78. The means provided includes a magnahelic gauge (not shown) for measuring the differential pressure across the HEPA filter 78. When the differential pressure exceeds a selected amount, the gauge will illuminate a light (not shown) to indicate that the filter 78 should be changed.

As is shown in FIG. 1, the apparatus 10 includes a threaded rod 86 extending upwardly from the upper end of the light fixture 70 and along the vertical axis 18 of the housing 14. A bracket 90, having therein a centrally located throughbore, is mounted on the threaded rod 86 and engages the upper end of the HEPA filter 78 to secure the filter 78 in place. The bracket 90 seals the upper end of the filter 78 and prevents air from bypassing the filter by flowing through the upper end of the filter. A nut 94 is threaded onto the threaded rod 86 to secure the bracket 90 into place.

The apparatus 10 also includes an activated carbon or charcoal filter 98 mounted in the housing 14 above the upper end of the HEPA filter 78. The filter 98 controls odor and is selectively removable so that it can be replaced when its useful life is exhausted. The filter 98 extends across the air flow path so that air entering the housing 14 must pass through the filter 98.

The apparatus 10 also includes a prefilter 102 mounted in the housing 14 above the filter 98. The prefilter 102 is also mounted across the air flow path so that any air entering the apparatus 10 must pass through the prefilter 102. The prefilter 102 removes the large particles from the incoming air and takes the burden off of the charcoal filter 98 and the HEPA filter 78, thereby extending the useful life of the filters 78 and 98.

The apparatus 10 also includes a dome-shaped inlet grille 106 mounted on the upper end 22 of the housing 14. The grille 106 provides a three hundred and sixty degree inlet so that air enters the apparatus from all corners of the room. The grille 106 also provides an aesthetically pleasing finish to the apparatus 10. The inlet grille 106 is formed from a dome-shaped sheet of punched metal. The grille 106 is removable to allow servicing of the apparatus 10. An electrical lockout is provided to prevent activation of the UV light 74 during servicing of the unit. Preferably, the lockout includes (see FIG. 4) a switch 110 which is electrically connected between the power circuit 62 of the apparatus 10 and the UV light fixture 70. The switch 110 is physically mounted between the housing 14 and the grille 106 so that when the inlet grille 106 is removed, the switch 110 is electrically opened and prevents power from reaching the UV light 74.

An electrical lockout is preferably also provided to prevent operation of the apparatus 10 if the filter 78 is not in place. This lockout can include the switch 110, which can be positioned so as to be opened if either the grille 106 is removed or the filter 78 is not in place. In this case the switch 110 would have to be located in the power circuit so as to disable the entire apparatus when the switch 110 is open.

The apparatus 10 also includes (see FIG. 3) a removable dome-shaped cover 114 for the inlet grille 106. The cover 114 includes a cover inlet 118 communicating with an inlet conduit 122. The inlet conduit 122 communicates with the exterior of the room, and the cover 114 is placed over the inlet grille 106 to create a positive pressure in the room in a manner which will be described below in more detail.

In operation, when the unit is turned on, air passes through the dome-shaped inlet grille 106 and into the housing 14 through the prefilter 102 and the activated carbon filter 98. The air then passes through the HEPA filter 78 into the chamber housing the UV light 74. The air then passes down through the opening defined by the lower end of the HEPA filter 78 and through the fan 54 and exits the apparatus 10 through the outlet grille 34.

The unit is convertible so that it may be used to create either a negative pressure or a positive pressure in a room simply by connection of the appropriate cover on the inlet grille 106 or the outlet grille 34. Specifically, with the annular cover 42 on the outlet grille 34, air in the room will enter the inlet grille 106 and follow the air flow path through the apparatus 10 so that the air is exhausted through the outlet cover 42 and the outlet conduit 50 to the exterior of the room. In this manner, air is continuously being pumped out of the room to create a negative pressure in the room relative to adjacent rooms.

Alternatively, with the dome-shaped cover 114 on the inlet grille 106, air will be drawn from the exterior of the room through the inlet conduit 122 and the cover inlet 118 and into the housing. The air will follow the air flow path and be exhausted into the room via the outlet grille 34. In this manner, exterior air is continuously being drawn into the room to create a positive pressure in the room relative to adjacent rooms.

In an alternative embodiment (not shown), the apparatus can be made convertible by internal valves rather than the covers 42 and 114. One valve would switch air flow between the inlet conduit 122 and the inlet grille 106, and the other valve would switch air flow between the outlet conduit 50 and the outlet grille 34.

Various features of the invention are set forth in the following claims.

We claim:

1. A portable apparatus for creating a negative pressure in and filtering the air in a room, said apparatus comprising
    a generally cylindrical housing having a generally vertical axis and upper and lower ends, said housing defining an air flow path between said upper and lower ends, and said housing containing, within said air flow path, an annular HEPA filter with a lower end having therein an outlet, said filter being centered generally on said axis, a UV light source located inside said annular filter, and a fan located below said outlet of said annular filter,
    a dome-shaped inlet grille mounted on said upper end of said housing and centered on said housing axis,
    a cylindrical outlet grill mounted on said lower end of said housing and centered on said housing axis,
    an annular cover for said outlet grill, said cover having therein a cover outlet,
    an outlet conduit which communicates with said cover outlet and which is adapted to communicate with the exterior of the room, and
    rollers supporting said lower end of said housing for movement on the floor of the room,
    said fan causing air flow from the room into said housing through said inlet grille, through said annular filter in adjacent to said UV light source, through said annular filter outlet, through said outlet grille and said cover outlet, and through said outlet conduit to the exterior of the room.

2. An apparatus as set forth in claim 1 and further comprising a prefilter located above said annular filter.

3. An apparatus as set forth in claim 2 wherein said housing also contains, in said air flow path, a carbon filter adjacent said prefilter.

4. An apparatus as set forth in claim 1 wherein said inlet grille is removable from said housing to provide access to said annular filter, and wherein said annular filter is removable from said housing.

5. An apparatus as set forth in claim 1 and further comprising means for providing an indication of inadequate air flow through said filter.

6. An apparatus as set forth in claim 5 wherein said means includes a magnahelic gauge.

7. An apparatus as set forth in claim 1 wherein the height of said apparatus is adjustable to the applicable breathing zone.

8. An apparatus as set forth in claim 1 wherein said housing includes means for providing access to said annular filter, and wherein said apparatus further comprises means for preventing activation of said UV light source when said annular filter is accessed.

9. An apparatus as set forth in claim 1 wherein said housing includes means for providing access to said annular filter, and wherein said apparatus further comprises means for preventing operation of said apparatus when said annular filter is not in place.

10. An apparatus as set forth in claim 1 wherein housing has thereon at least one handle allowing said apparatus to be picked up.

11. An apparatus as set forth in claim 1 wherein said fan is a variable-speed fan so that said apparatus is adjustable for different size rooms.

12. An apparatus as set forth in claim 1 wherein said apparatus weighs less than 100 pounds and has a height of six feet or less and a diameter of less than two feet.

13. An apparatus as set forth in claim 1 wherein said inlet grille is the sole passageway for air to enter said housing and said outlet conduit is the sole passageway for air to exit said housing.

14. A portable apparatus for creating a negative pressure in and filtering the air in a room, said apparatus comprising
    a generally cylindrical housing having a generally vertical axis and tipper and lower ends, said housing defining an air flow path between said tipper and lower ends, and said housing containing, within said air flow path, an annular HEPA filter with a lower end having therein an outlet, said filter being centered generally on said axis, a UV light source located inside said annular filter, and a fan located below said outlet of said annular filter,
    a dome-shaped inlet grille mounted on said upper end of said housing and centered on said housing axis, an outlet conduit which communicates with said lower end of said housing and which is adapted to communicate with the exterior of the room, and rollers supporting said lower end of said housing for movement on the floor of the room, said fan causing air flow from the room into said housing through said inlet grille, through said annular filter adjacent to said UV light source, through said annular filter outlet, and through said outlet conduit to the exterior of the room, said apparatus being convertible to an apparatus for creating a positive pressure in the room, and said apparatus further comprising a cylindrical outlet grille mounted on said lower end of said housing and centered on said housing axis, a dome-shaped cover for said inlet grille, said cover having therein an inlet, and an inlet conduit which communicates with said cover inlet and which is adapted to communicate with the exterior of the room, such that when said outlet conduit is removed and said cover is placed over said inlet grille, air flows from the exterior of the room into said housing through said inlet conduit, through said inlet grille, through said annular filter adjacent to said UV light source, through said annular filter outlet, and through said outlet grille into the room.

15. A portable, convertible apparatus for creating either a negative pressure or a positive pressure in and filtering the air in a room, said apparatus comprising a housing having opposite upper and lower ends, said housing defining an air flow path between said upper and lower ends, and said housing containing, within said air flow path, a HEPA filter, and a fan, an inlet grille mounted on one of said ends of said housing, an outlet grille mounted on the other of said ends of said housing, an outlet cover for said outlet grille, said outlet cover having therein an outlet, an outlet conduit which communicates with said outlet of said outlet cover and which is adapted to communicate with the exterior of the room, an inlet cover for said inlet grille, said inlet cover having therein an inlet, and an inlet conduit which communicates with said inlet of said inlet cover and which is adapted to communicate with the exterior of the room, said apparatus being operable to create a negative pressure in the room when said outlet cover is placed over said outlet grille and said inlet cover is removed, said fan causing air flow from the room into said housing through said inlet grille, through said filter, and through said outlet conduit to the exterior of the room, said apparatus being operable to create a positive pressure in the room when said outlet cover is removed and said inlet cover is placed over said inlet grille, said fan causing air flow from the exterior of the room into said housing through said inlet conduit, through said inlet grille, through said filter, and through said outlet grille into the room.

16. An apparatus as set forth in claim 15 wherein said housing has upper and lower ends, wherein said inlet grille is mounted on said upper end of said housing, and wherein said outlet grille is mounted on said lower end of said housing.

17. An apparatus as set forth in claim 16 wherein said inlet grille is dome-shaped.

18. An apparatus as set forth in claim 17 wherein said outlet grille is cylindrical.

19. A portable, convertible apparatus for creating either a negative pressure or a/positive pressure in and filtering the air in a room, said apparatus comprising a generally cylindrical housing having a generally vertical axis and opposite upper and lower ends, said housing defining an air flow path between said upper and lower ends, and said housing containing, within said air flow path, an annular HEPA filter with a lower end having therein an outlet, said filter being centered on said housing axis, a UV light source located inside said annular filter, and a fan located below said outlet of said annular filter, a dome-shaped inlet grille mounted on said upper end of said housing and centered on said housing axis, a cylindrical outlet grille mounted on said lower end of said housing and centered on said housing axis, an outlet cover for said outlet grille, said outlet cover having therein an outlet, an outlet conduit which communicates with said outlet of said outlet cover and which is adapted to communicate with the exterior of the room, an inlet cover for said inlet grille, said inlet cover having therein an inlet, and an inlet conduit which communicates with said inlet of said inlet cover and which is adapted to communicate with the exterior of the room, said apparatus being operable to create a negative pressure in the room when said outlet cover is placed over said outlet grille and said inlet cover is removed, said fan causing air flow from the room into said housing through said inlet grille, through said filter, and through said outlet grille and said outlet conduit to the exterior of the room, said apparatus being operable to create a positive pressure in the room when said outlet cover is removed and said inlet cover is placed over said inlet grille, said fan causing air flow from the exterior of the room into said housing through said inlet conduit and said inlet grille, through said filter, and through said outlet grille into the room.

* * * * *